US010219800B2

(12) United States Patent
Tsubouchi

(10) Patent No.: US 10,219,800 B2
(45) Date of Patent: Mar. 5, 2019

(54) MINIMALLY-INVASIVE SURGERY TOOL WITH AUTOMATIC LIGHTING

(71) Applicant: Terumo Cardiovascular Systems Corporation, Ann Arbor, MI (US)

(72) Inventor: Takeshi Tsubouchi, Dexter, MI (US)

(73) Assignee: TERUMO CARDIOVASCULAR SYSTEMS CORPORATION, Ann Arbor, MI (US)

( * ) Notice: Subject to any disclaimer, the term of this patent is extended or adjusted under 35 U.S.C. 154(b) by 0 days.

(21) Appl. No.: 15/670,449

(22) Filed: Aug. 7, 2017

(65) Prior Publication Data

US 2018/0042596 A1  Feb. 15, 2018

Related U.S. Application Data

(60) Provisional application No. 62/372,335, filed on Aug. 9, 2016.

(51) Int. Cl.
| *A61B 17/02* | (2006.01) |
| *A61B 5/00* | (2006.01) |
| *A61B 90/30* | (2016.01) |
| *A61B 90/60* | (2016.01) |
| *A61B 17/00* | (2006.01) |

(52) U.S. Cl.
CPC ........ *A61B 17/0218* (2013.01); *A61B 5/0082* (2013.01); *A61B 17/02* (2013.01); *A61B 17/0206* (2013.01); *A61B 90/30* (2016.02); *A61B 5/0077* (2013.01); *A61B 5/0084* (2013.01); *A61B 90/60* (2016.02); *A61B 2017/00734* (2013.01); *A61B 2017/0237* (2013.01); *A61B 2090/309* (2016.02)

(58) Field of Classification Search
CPC ............ A61B 17/0218; A61B 17/0206; A61B 17/0293; A61B 17/02; A61B 5/0082; A61B 5/0077; A61B 5/0084; A61B 90/60; A61B 90/36; A61B 1/0684; A61B 1/0676; A61B 1/32; A61B 1/00032; A61B 2090/309; A61B 2017/00734
USPC .................... 600/217, 245, 232, 201, 214, 1
See application file for complete search history.

(56) References Cited

U.S. PATENT DOCUMENTS

| 4,726,356 A | 2/1988 | Santilli et al. |
| 4,865,019 A | 9/1989 | Phillips |
| 5,772,583 A | 6/1998 | Wright et al. |
| 6,428,180 B1* | 8/2002 | Karram ................ A61B 5/0059 |
| | | 362/109 |
| 9,730,685 B2* | 8/2017 | Wan ........................ A61B 1/32 |
| 2004/0030223 A1 | 2/2004 | Calafiore et al. |

(Continued)

*Primary Examiner* — Pedro Philogene
(74) *Attorney, Agent, or Firm* — Darryl Newell; MacMillan, Sobanski & Todd, LLC

(57) ABSTRACT

A surgical device provides a retractor tool or rake with integral lighting. The device includes a retractor body having a rake finger at one end and a handle at its other end. A light source is embedded in the rake finger. A power unit supplies a current to the light source, and a cable interconnects the retractor body and the power unit. Sterile packaging is adapted to contain the surgical device, wherein the sterile packaging has a deactivation feature for preventing the supplying of current from the power unit to the light source while the device is stored within the sterile packaging, and wherein removal of the device from the sterile packaging results in automatically supplying the current to the light source.

13 Claims, 9 Drawing Sheets

(56) References Cited

U.S. PATENT DOCUMENTS

| | | |
|---|---|---|
| 2006/0100487 A1 | 5/2006 | Cartier et al. |
| 2007/0060795 A1* | 3/2007 | Vayser .................... A61B 1/32 600/245 |
| 2008/0108877 A1* | 5/2008 | Bayat ..................... A61B 17/02 600/214 |
| 2014/0012090 A1* | 1/2014 | Heitland ................ A61B 17/02 600/217 |

* cited by examiner

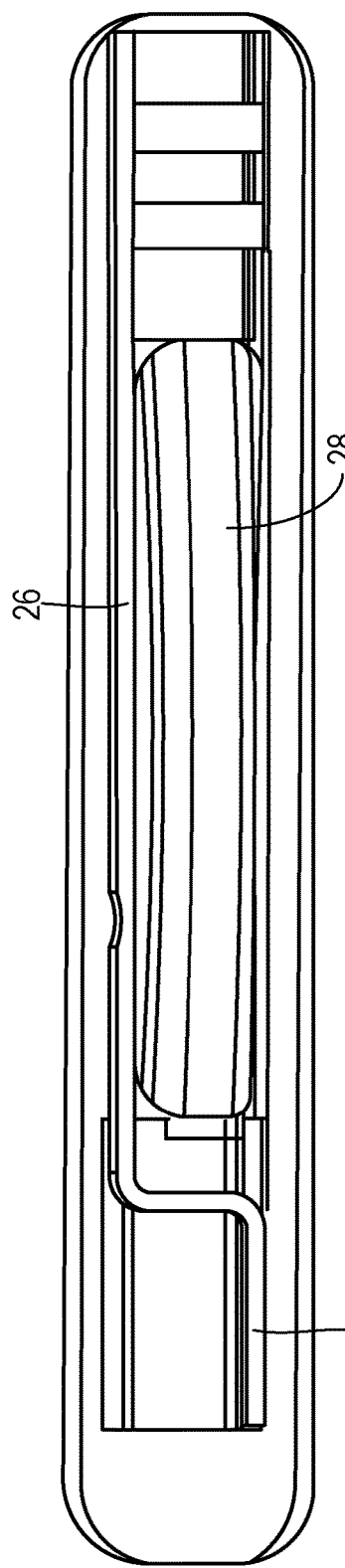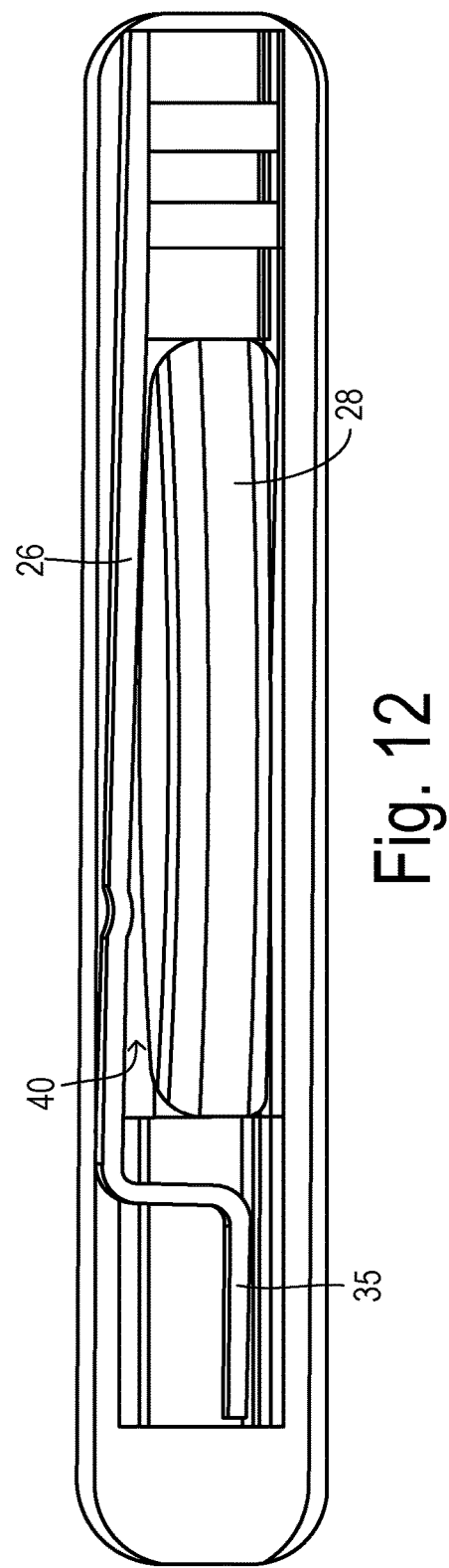

MINIMALLY-INVASIVE SURGERY TOOL WITH AUTOMATIC LIGHTING

CROSS REFERENCE TO RELATED APPLICATIONS

This application claims priority to provisional application Ser. No. 62/372,335, filed on Aug. 9, 2016, which is incorporated herein by reference in its entirety.

BACKGROUND OF THE INVENTION

The present invention relates in general to surgical retractor tools, and, more specifically, to a disposable retractor tool or rake with integral lighting which can be manipulated manually as a "one-finger assistant" or can be suspended from a support frame.

In certain surgical procedures, such as minimally-invasive cardiac surgery (MICS), access into a patient's body is obtained through a relatively small incision in order to reduce recovery times and tissue trauma. In order to manipulate tissues and perform the desired surgical operation deep inside the patient's body through the small incision, various tools are necessary.

One such tool is a rake which may include paddle-like flat or curved surfaces (or wire-frame constructions) for retracting, lifting, or positioning various tissues such as the heart or a heart valve. The tool may be handheld or may be adapted to be mounted to a support frame that holds the tool at a selected position.

One example of a surgical procedure requiring a handheld tool in particular, is an operation to remove a portion of a thickening heart septum through the aortic valve. In this procedure, it is necessary to support the valve and keep it open during access to the septum. Because of the narrow entry and the depth at which the surgeon performs an operation such as this one, obtaining sufficient illumination of the target tissues can be difficult. A typical light source is mounted externally of the surgical site, such as a light supported by a head band worn by the surgeon or a light suspended on a movable support arm from a fixed frame. Light penetration is limited, and shadowing may often occur.

SUMMARY OF THE INVENTION

The invention provides a disposable, sterile tool with an integral light source that enters the surgical site for shadowless and bright illumination. The light source and electrical wiring are embedded in the tool in order to provide electrical isolation for the patient and to prevent moisture from reaching the electrical components. To maximize user convenience and facilitate sterility, the tool automatically illuminates as a result of being removed from its sterile packaging.

BRIEF DESCRIPTION OF THE DRAWINGS

FIGS. 11 and 12 are side views of a battery unit in a powered and unpowered state, respectively.

DETAILED DESCRIPTION OF PREFERRED EMBODIMENTS

Figure 1:
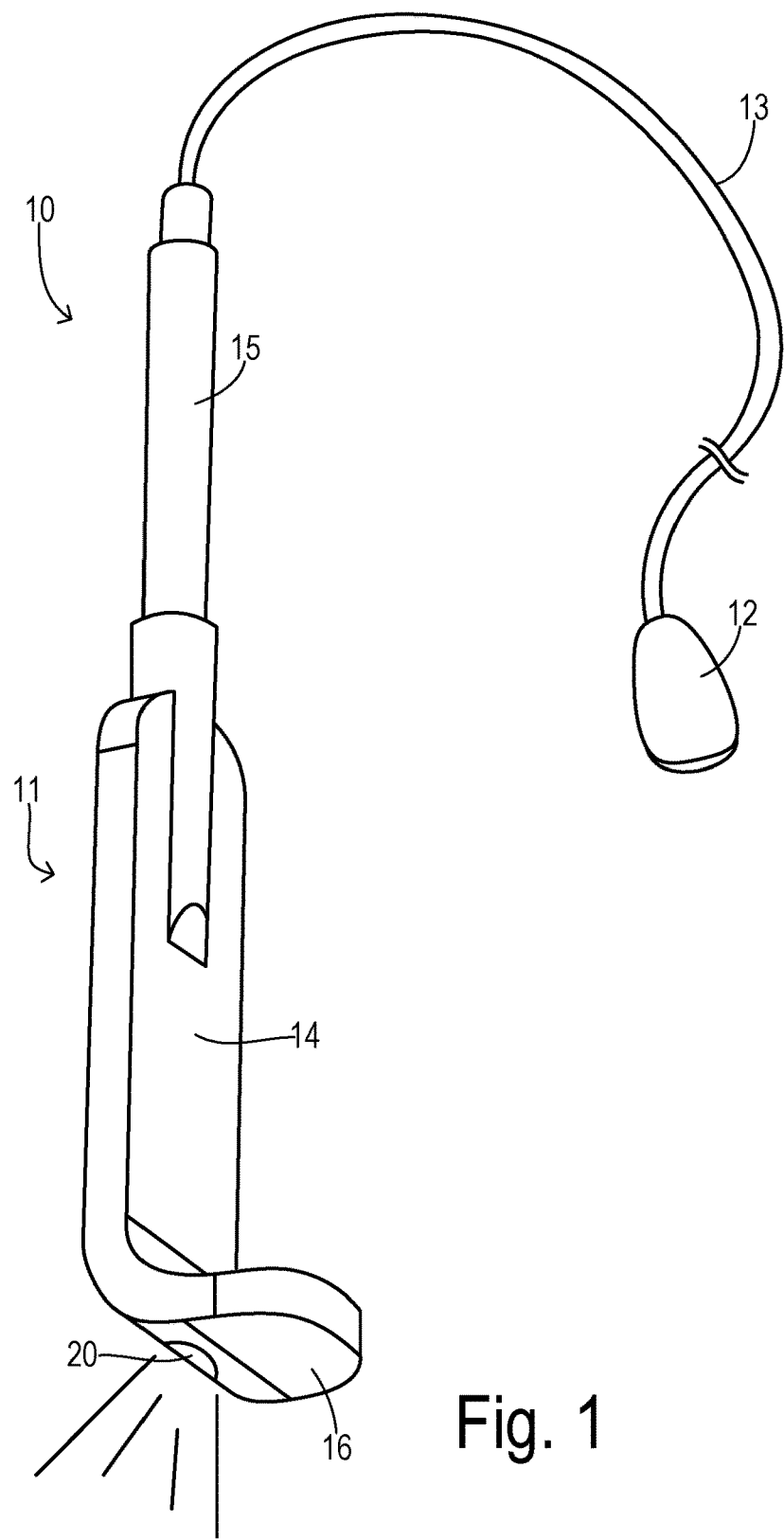
FIGS. 1 and 2 are perspective views of one preferred embodiment of an illuminated retractor tool and power supply.
Figure 2:
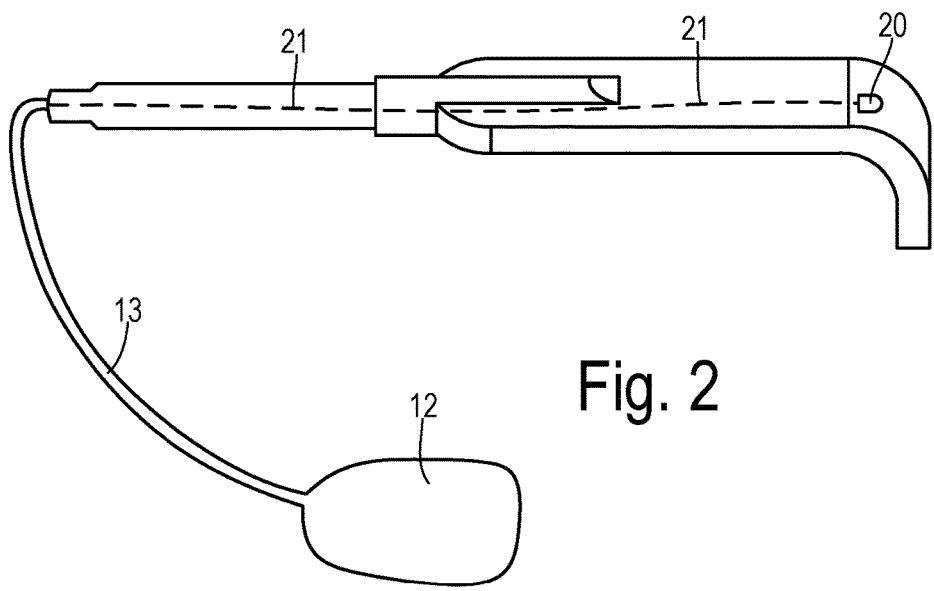

FIGS. 1 and 2 are perspective views of an illuminated tool system 10 having a retractor or rake body 11 connected to a power unit 12 by a power cord 13. Rake body 11 has a paddle or rake 14 and a handle section 15 at opposite ends. Rake 14 is formed at the distal end with a finger or flap 16 extending transversely from body 11. Rake body 11 is preferably molded of a biocompatible thermoplastic material such as polyvinylchloride, nylon, or the like. At least in the region of rake 14, body 11 is comprised of a light transmissive (i.e., clear) plastic. A light emitting diode (LED) 20 and electrical wiring 21 are imbedded by insert molding rake body 11 around them or by potting. LED 20 preferably emits white light. Other light sources could also be used. Power unit 12 supplies a current to LED 20 that produces a desired level of illumination. Wiring 21 passes through power cord or cable 13 to power unit 12 with the overmolding preferably forming a continuously molded structure for hermetically sealing the internal components in order to maintain sterility.

Handle section 15 can be held manually by a user to insert the distal end of finger 16 through a surgical incision to manipulate tissue. Handle section 15 can also be configured to attach to an adjustable support arm. The support arm could be the Hercules™ Stabilizing Arm, available from Terumo Cardiovascular Systems Corporation of Ann Arbor, Michigan. The support arm could itself be mounted to a sternal retractor frame in the case of cardiac surgery, as known in the art.

Figure 3:
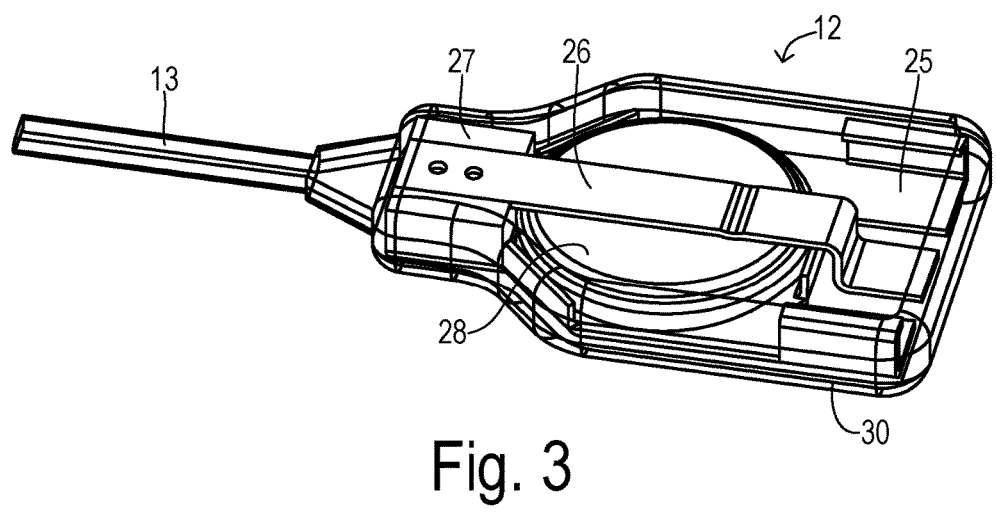
FIGS. 3 and 4 are perspective views of a battery unit according to one preferred embodiment of the invention.
Figure 4:
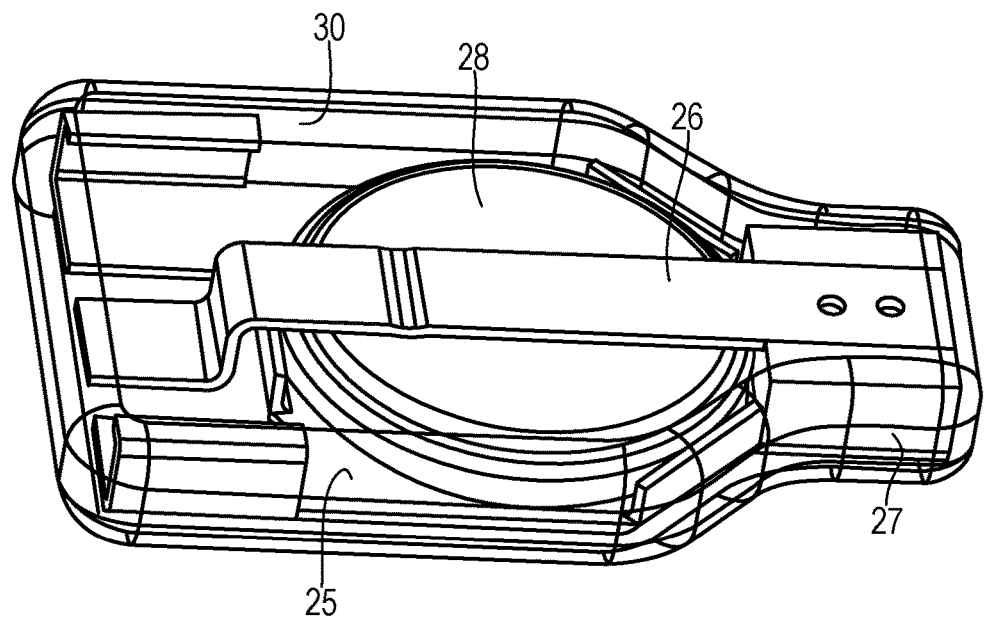

FIGS. 3 and 4 show battery power unit 12 in greater detail. Power unit 12 includes a bottom plate 25, a top plate 26, a spacer 27, a battery 28, and an overmolded body 30 encapsulating the other elements and preferably comprising a soft, flexible material such as silicon rubber. Overmold body 30 is shown in phantom so that the internal elements can be seen, but it preferably completely surrounds the other elements after they are assembled. An open space or bubble (not shown) may preferably be formed in overmold body 30 above top plate 26 to facilitate movement of top plate 26 off of battery 28 to disconnect LED 20 from power as described below, but a space is not necessary if body 30 can be sufficiently stretched.

Figure 5:
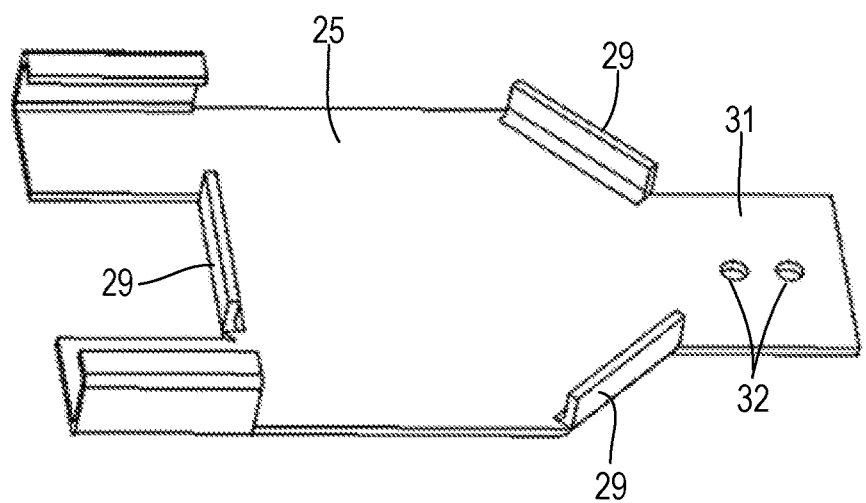
FIG. 5 is a perspective view of a bottom plate of the battery unit of FIGS. 3 and 4.
Figure 6:
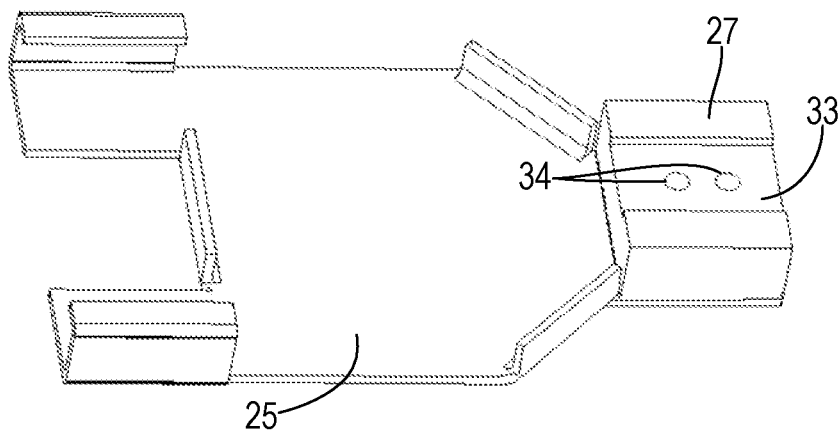
FIGS. 6 and 7 are perspective views showing addition of a spacer and an upper plate to the bottom plate, respectively.

As shown in FIG. 5, bottom plate 25 is comprised of a conductive metal sheet formed with retaining walls 29 to receive battery 28, thereby forming a connection to one side of battery 28. Bottom plate 25 has a lateral tongue 31 that receives insulating spacer 27 as shown in FIG. 6. Tongue 31 may have holes 32 for receiving mating projections (not shown) of spacer 27 in order to mount spacer 27 by heat staking or interference fit, for example. Other means of fastening such as adhesives or screws may also be employed.

Figure 7:
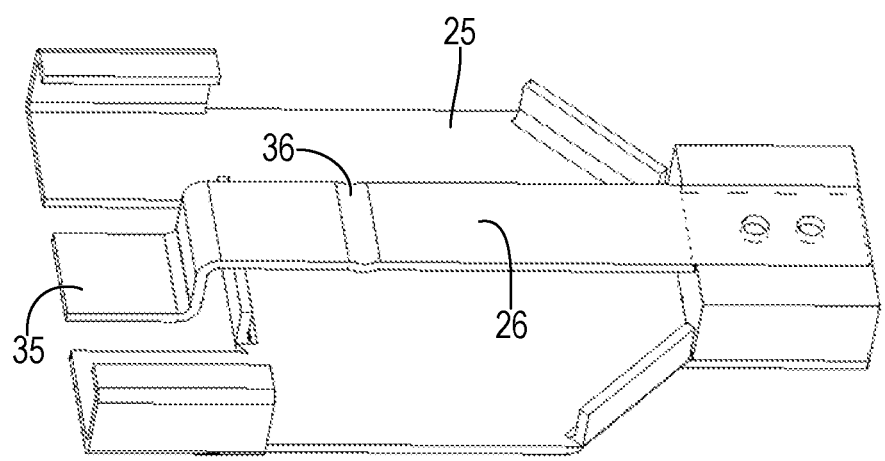
Figure 8:
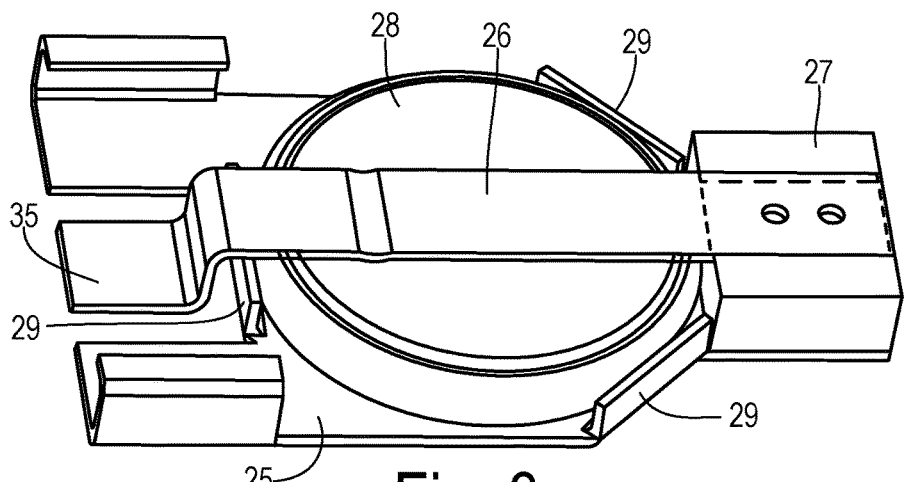
FIG. 8 shows a battery inserted in the assembly of FIG. 7.

Spacer 27 has an upper groove 33 for receiving one end of top plate 26 as shown in FIGS. 6 and 7. Spacer 33 may include projections 34 to facilitate mounting to matching holes in top plate 26. Top plate 26 has a remote end 35 suspended as a cantilever over one side of battery 28 as shown in FIG. 8. Battery 28 is snapped into place between walls 29. Top plate 26 may have a dimple or bar 36 to make firm electrical contact with battery 28. In its normal relaxed position, top plate 26 urges against battery 28. Wires 21 are connected to plates 25 and 26 (e.g., by soldering, not shown) so that when top plate 26 is in its normal position, an electrical circuit is completed so that LED 20 is activated. By pressing remote end 35 upward (i.e., perpendicular to bottom plate 25), plate 26 can be separated from battery 28 and the electrical circuit is deactivated.

Figure 9:
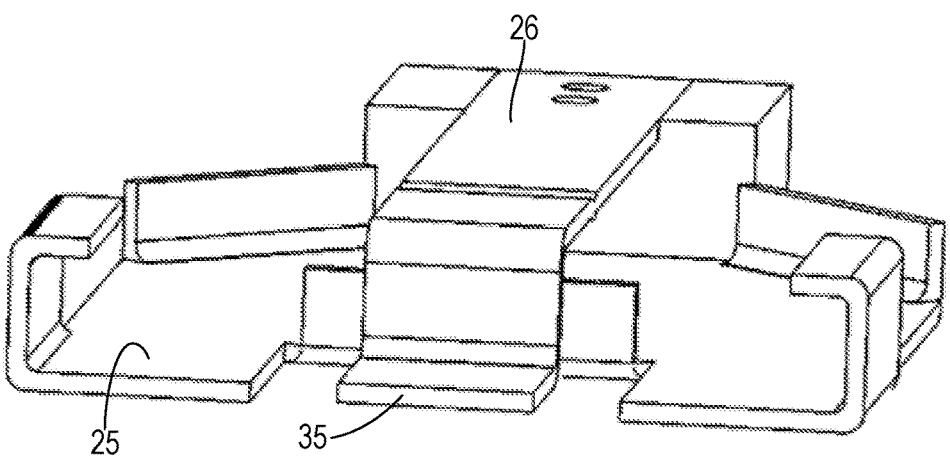
FIGS. 9 and 10 are end views of the assembly of FIG. 7 showing a rest position and a deflected position of the upper plate, respectively.
Figure 10:
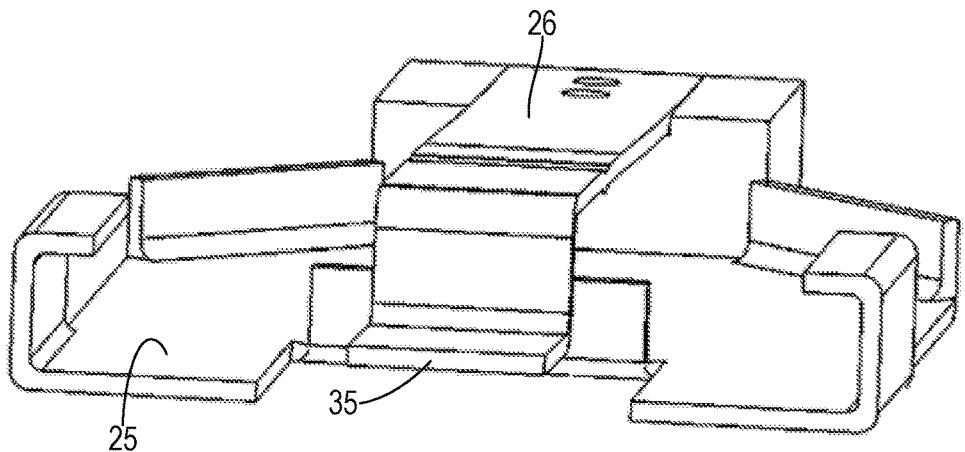

FIGS. 9 and 10 show top plate 26 in its normal position and its deflected position, respectively. Likewise, the side views in FIGS. 11 and 12 show top plate 26 in its normal position and its deflected position, respectively. In the deflected position, a gap 40 is created between battery 28 and top plate 26 so that the LED is switched off.

Figure 13:
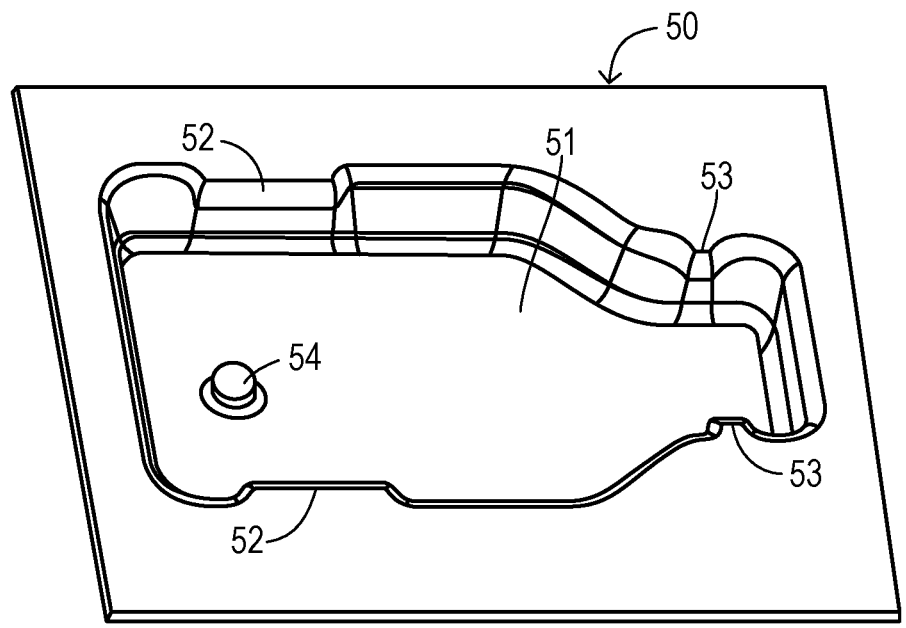
FIG. 13 is a perspective view of a sterile packaging tray.
Figure 14:
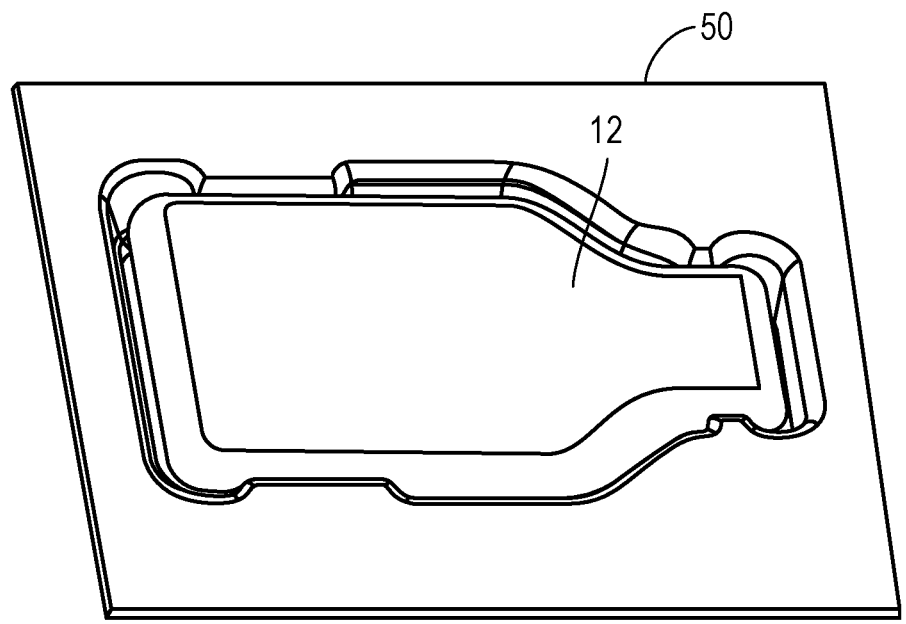
FIG. 14 is a perspective view of the battery unit inserted in the sterile packaging tray.
Figure 15:
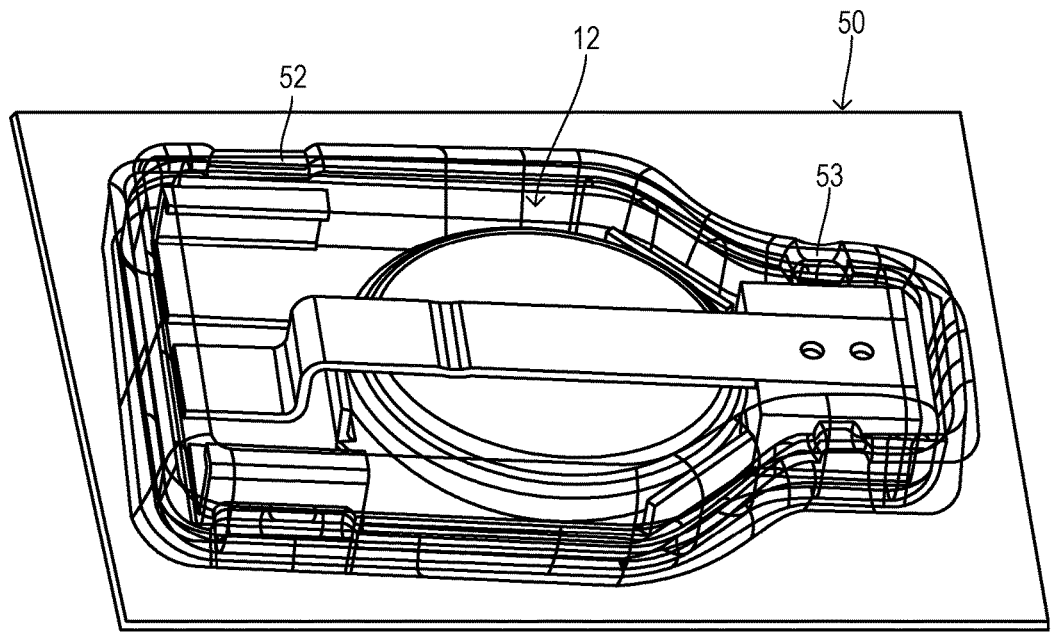
FIG. 15 is another perspective view of the battery unit inserted in the sterile packaging tray showing internal elements of the battery unit.

The sterile packaging for the tool system of the invention may include a tray 50 shown in FIG. 13. A receptacle 51 is formed as a depression into tray 50 with a shape configured to receive the power unit. Receptacle 51 may preferably also accommodate at least a portion of the power cord and/or a transition section that connects the power cord to the power unit (not shown). A plurality of snap tabs 52 and 53 are provided along the periphery of receptacle 51 so that power unit 21 can be selectably retained in the receptacle as shown in FIGS. 14 and 15.

Figure 16:
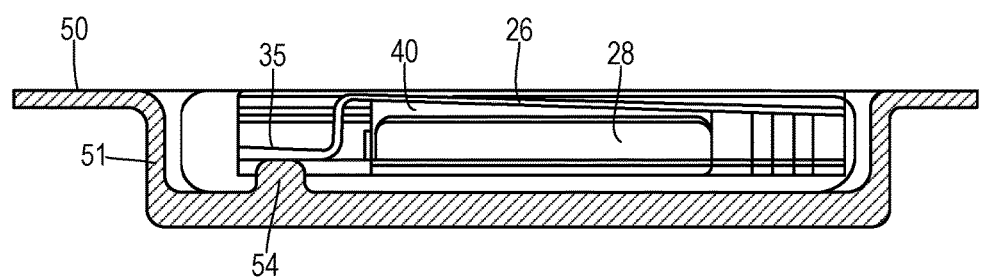
FIG. 16 is a side view cross-sectional view of the assembly of FIG. 15.

A protuberance 54 extends upward from a bottom floor of receptacle 51 to act as a thrust knob or other deactivation feature to push against the cantilevered end 35 of the top plate 26 when power unit 21 is installed in receptacle 51. The interaction of protuberance 54 with top plate 26 is shown in FIG. 16. After assembly of the tool system and mounting in the sterile packaging, the LED is turned off and battery energy is conserved until the tool system is opened and used. As soon as power unit 21 is removed from receptacle 51, the LED is instantly illuminated without requiring manual operation of any switch.

With the LED illuminated, a surgeon can manipulate the tool grasping the handle so that the rake is inserted through an incision, and light is brought directly to the areas that need to be visualized during a procedure. The handle could also be adapted to be mounted onto a frame or other supporting structure so that it can provide a hands-free retraction function together with automatic, localized illumination.

Figure 17:
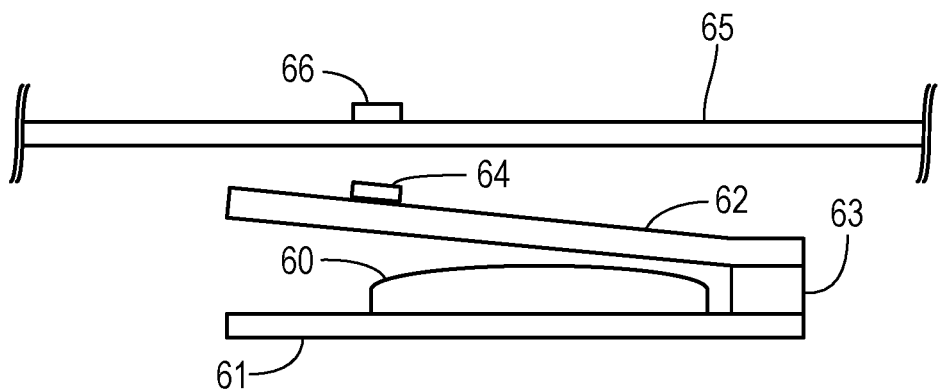
FIG. 17 is a side view of a battery unit and packaging tray according to an alternative embodiment wherein battery power is disconnected magnetically.

Instead of a mechanically-operated switch, the present invention can use other types of deactivation feature for keeping the LED turned off while in the sterile packaging and for automatically connecting the battery to the LED when removed from the packaging. For example, a magnetic switch could be provided as shown in FIG. 17 wherein a battery 60 is mounted to a conductive metal bottom plate 61. A conductive metal top plate 62 is mounted to bottom plate 61 by an insulating block 63. As in the previous embodiment, the plates and battery may be encased in a soft, flexible overmolded body (not shown) which allows top plate 62 to bend in a manner that disconnects it from battery 60. A magnet 64 is affixed to top plate 62 near the movable end. A packaging tray 65 has a magnet 66 affixed at a location adjacent magnet 64 and having a polarity that provides a force of attraction between magnets 64 and 66. With the power unit installed in tray 65, the magnetic attraction is sufficient to bend top plate 62 away from battery 60, resulting in disconnection of battery 60 from the LED (not shown). After removing the power unit from tray 65, top plate 62 springs back into contact with battery 60 so that the LED is automatically activated. Of course, either one of magnets 64 or 66 could be replaced with ferritic iron.

Figure 18:
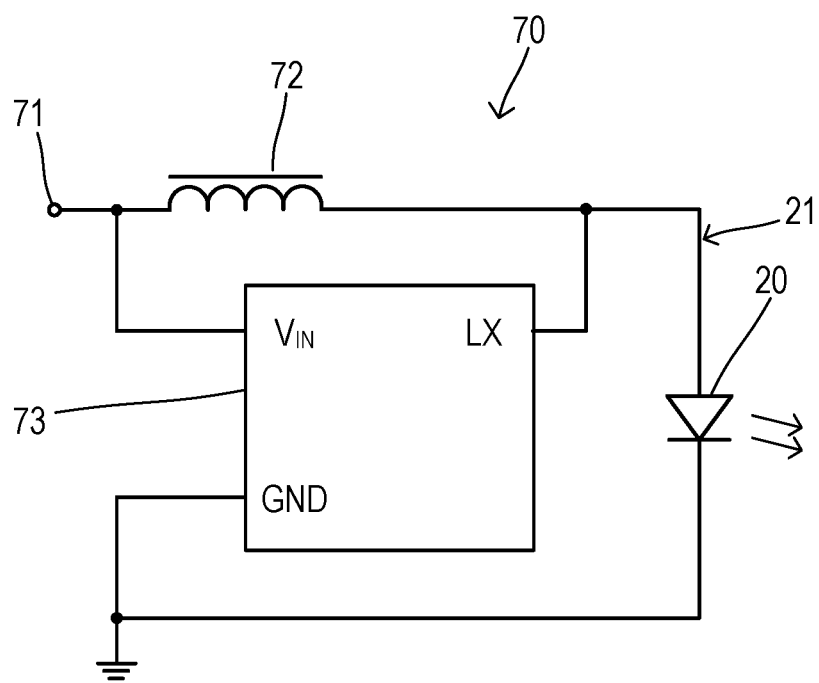
FIG. 18 is a schematic diagram showing an LED driver circuit useful for the present invention.

FIG. 18 shows an LED driver circuit 70 which may preferably be incorporated within the battery power unit (e.g., interconnected with wires 21 and encased in the overmold body) to deliver an appropriate drive signal to LED 20. An input terminal 71, which is connected to receive battery power (not shown) when the power unit is removed from the sterile packaging, is coupled to the anode of LED 20 via an inductor 72 and is connected to a $V_{IN}$ terminal of an integrated circuit 73. Inductor 72 may have a value of about 47 µH. Integrated circuit 73 may be comprised of an LED lamp driver integrated circuit such as the CL0118B device available from ChipLink Semiconductor Co. Ltd., for example. An output terminal LX is connected to a junction between inductor 72 and the anode of LED 20. Inductor 72 and IC 73 supply a constant current to LED 20 based on the DC voltage from the battery (e.g., about 3 V). The small size of IC 73 and inductor 72 allows the circuit to be easily integrated into the overmolded body of the power unit.

What is claimed is:

1. A retractor tool for minimally-invasive surgery comprising:
    a rake body;
    an LED and wiring embedded into the rake body;
    a power unit attached via a cable to the LED and wiring, wherein the power unit includes a flexible molded body containing a bottom plate for holding a battery and a movable top plate for selectably connecting to the battery to turn the LED on and off; and
    a tray for sterile packaging of the tool and having a receptacle for the power unit with a protuberance for pushing the top plate off of the battery.

2. The tool of claim 1 wherein the LED and wiring are insert molded into the rake body.

3. The tool of claim 1 wherein the LED and wiring are potted into the rake body.

4. A surgical device comprising:
    a retractor body having a rake finger at one end and a handle at its other end;
    a light source embedded in the rake finger;
    a power unit for supplying a current to the light source;
    a cable interconnecting the retractor body and the power unit; and
    sterile packaging adapted to contain the surgical device, wherein the sterile packaging has a deactivation feature for preventing the supplying of current from the power unit to the light source while the device is stored within the sterile packaging, and wherein removal of the device from the sterile packaging results in automatically supplying the current to the light source.

5. The surgical device of claim 4 wherein the light source is an LED.

6. The surgical device of claim 4 wherein the retractor body is comprised of a light transmissive plastic, and wherein the LED is insert molded into the retractor body so that the LED is hermetically sealed.

7. The surgical device of claim 4 wherein a distal end of the rake finger extends transversely to the handle.

8. The surgical device of claim 4 wherein the handle is configured to attach to an adjustable support arm.

9. The surgical device of claim 4 wherein the power unit comprises a battery, wherein the sterile packaging is comprised of a tray having a receptacle for the power unit, and wherein the deactivation feature is comprised of a protuberance within the receptacle for pushing a movable conductor in the power unit that disconnects the battery.

10. The surgical device of claim 4 wherein the power unit comprises a battery and a movable conductor plates having a rest position that connects the battery and a deflected position that disconnects the battery, wherein the sterile packaging is comprised of a tray having a receptacle for the power unit, and wherein the deactivation feature is comprised of a magnetic element within the receptacle for attracting the movable conductor plate into the deflected position.

11. A retractor tool for minimally-invasive surgery comprising:
   a rake body;
   an LED and wiring embedded into the rake body;
   a power unit attached via a cable to the LED and wiring, wherein the power unit includes a flexible molded body containing a bottom plate for holding a battery and a movable top plate for selectably connecting to the battery to turn the LED on and off; and
   a tray for sterile packaging of the tool and having a receptacle for the power unit with a protuberance for pushing the top plate off of the battery.

12. The tool of claim 11 wherein the LED and wiring are insert molded into the rake body.

13. The tool of claim 11 wherein the LED and wiring are potted into the rake body.

* * * * *